(12) United States Patent
Krysztof et al.

(10) Patent No.: US 7,441,629 B2
(45) Date of Patent: Oct. 28, 2008

(54) STETHOSCOPE WITH IDENTIFYING-PERSONALIZING RING

(75) Inventors: Andrzej Krysztof, deceased, late of Lomianki (PL); by Joanna Magdalena Brudkiewicz-Krysztof, legal representative, Ul. Podbipiety 10, PL-05092 Lomianki (PL); Adam Rajmund Krysztof, Ul. Podbipiety 10, PL-05092 Lomianki (PL); Michal Jan Krysztof, Ul. Podbipiety 10, PL-05092 Lomianki (PL)

(73) Assignees: Joanna Magdalena Brudkiewicz-Krysztof, Lomianki (PL); Adam Rajmund Krysztof, Lomianki (PL); Michal Jan Krysztof, Lomianki (PL)

( * ) Notice: Subject to any disclaimer, the term of this patent is extended or adjusted under 35 U.S.C. 154(b) by 282 days.

(21) Appl. No.: 10/567,556

(22) PCT Filed: Aug. 10, 2004

(86) PCT No.: PCT/PL2004/000064

§ 371 (c)(1), (2), (4) Date: Feb. 8, 2006

(87) PCT Pub. No.: WO2005/016148

PCT Pub. Date: Feb. 24, 2005

(65) Prior Publication Data

US 2006/0201738 A1    Sep. 14, 2006

(30) Foreign Application Priority Data

Aug. 14, 2003  (PL) .................................... 361686
Jul. 29, 2004   (PL) .................................... 369346

(51) Int. Cl.
     A61B 7/02    (2006.01)

(52) U.S. Cl. ........................................ 181/131; 600/528
(58) Field of Classification Search ................. 181/131; 600/528
     See application file for complete search history.

(56) References Cited

U.S. PATENT DOCUMENTS 1,894,381 A * 1/1933 Markle ..................... 137/364

(Continued)

OTHER PUBLICATIONS

The Twentieth Century, pp. 1-11 pertinent, close ups of pertinent images includes☐☐www.antiquemed.com/20th_century.htm.*

Primary Examiner—Lincoln Donovan
Assistant Examiner—Forrest Phillips
(74) Attorney, Agent, or Firm—Michael Bednarek; Paul, Hastings, Janofsky & Walker LLP

(57) ABSTRACT

A medical stethoscope head (1) comprises a body (2) with an inlet pipe and at least one diaphragm portion (4) provided with a diaphragm (5) at its lower surface. At least one identifying-personalizing ring (11) provided with identifying-personalizing means (14) is mounted in any area of an upper surface (10) of said diaphragm portion (4), opposite to said diaphragm (5). The identifying-personalizing ring (11), at its surface adjacent to the diaphragm portion (4), is provided with at least one locating element for explicit locating the identifying-personalizing ring (11) in defined angular position in relation to an axis (3') of said inlet pipe (3) of said body (2). In other embodiment of the invention a medical stethoscope head comprises a diaphragm portion (4), which, at its upper surface (10), opposite to a diaphragm (5), is provided with any identifying-personalizing means (14), and said diaphragm portion (4) is disconnectable joined with said body (2) by at least one locating-connecting means (20), allowing exchanging of a diaphragm portion (4) and explicit locating the diaphragm portion (4) in defined angular position in relation to an axis (3') of said inlet pipe (3) of said body (2).

7 Claims, 6 Drawing Sheets

U.S. PATENT DOCUMENTS

| | | | | |
|---|---|---|---|---|
| 2,061,215 | A * | 11/1936 | Taylor | 40/300 |
| 2,178,727 | A * | 11/1939 | Owens | 411/143 |
| 2,181,796 | A * | 11/1939 | Williams, Jr. | 40/634 |
| 3,187,452 | A * | 6/1965 | Dotson | 40/202 |
| 3,621,206 | A * | 11/1971 | Scribner | 235/485 |
| 4,280,293 | A * | 7/1981 | Kovalenko et al. | 40/587 |
| 4,497,124 | A * | 2/1985 | Olive | 40/299.01 |
| 5,190,354 | A * | 3/1993 | Levy et al. | 301/37.25 |
| D349,959 | S * | 8/1994 | Troiani | D24/134 |
| 5,420,382 | A * | 5/1995 | Katz | 181/131 |
| D381,367 | S * | 7/1997 | Rashman | D20/22 |
| 5,649,381 | A * | 7/1997 | Studer | 40/633 |
| 5,659,989 | A * | 8/1997 | Hsiao et al. | 40/587 |
| 5,673,503 | A * | 10/1997 | Rendleman | 40/27.5 |
| D390,607 | S * | 2/1998 | Rashman et al. | D20/25 |
| 5,747,752 | A * | 5/1998 | Selinger | 181/131 |
| 5,798,489 | A * | 8/1998 | Gillio | 181/131 |
| 5,847,330 | A * | 12/1998 | Grosslight | 181/131 |
| 5,957,542 | A * | 9/1999 | Boothe et al. | 301/37.25 |
| 6,003,260 | A * | 12/1999 | Chang | 407/748 |
| D422,701 | S * | 4/2000 | Gallagher | D24/134 |
| D423,099 | S * | 4/2000 | Gallagher | D24/134 |
| 6,119,381 | A * | 9/2000 | Grocholski | 40/405 |
| 6,165,035 | A * | 12/2000 | Avner | 446/72 |
| 6,269,573 | B1 * | 8/2001 | Najmi | 40/666 |
| 6,519,882 | B1 * | 2/2003 | Shuen | 40/209 |
| 6,520,639 | B2 * | 2/2003 | Avner | 351/205 |
| 6,694,651 | B1 * | 2/2004 | Shuen | 40/591 |
| 6,701,648 | B2 * | 3/2004 | Battaglia | 40/299.01 |
| 6,847,720 | B2 * | 1/2005 | Tseng | 381/67 |
| 6,857,709 | B1 * | 2/2005 | McLean et al. | 301/37.25 |
| 7,036,891 | B2 * | 5/2006 | Chen | 301/37.25 |
| 7,150,549 | B2 * | 12/2006 | Olds et al. | 362/500 |
| 7,234,257 | B2 * | 6/2007 | Bar-Yona | 40/454 |
| 2001/0013188 | A1 * | 8/2001 | Hall | 40/610 |
| 2002/0066219 | A1 * | 6/2002 | Weidman et al. | 40/913 |
| 2003/0000119 | A1 * | 1/2003 | Savy | 40/301 |
| 2003/0047376 | A1 * | 3/2003 | Oster et al. | 181/131 |
| 2003/0093932 | A1 * | 5/2003 | Battaglia, Jr. | 40/299.01 |
| 2003/0177678 | A1 * | 9/2003 | Sloot | 40/587 |
| 2003/0221903 | A1 * | 12/2003 | Roby et al. | 181/131 |
| 2004/0107610 | A1 * | 6/2004 | Gulati | 40/316 |
| 2004/0114767 | A1 * | 6/2004 | Tseng | 381/67 |
| 2004/0120781 | A1 * | 6/2004 | Luca et al. | 409/84 |
| 2004/0139642 | A1 * | 7/2004 | Johnsen et al. | 40/661.11 |
| 2006/0201738 | A1 * | 9/2006 | Krysztof | 181/131 |
| 2007/0058818 | A1 * | 3/2007 | Yoshimine | 381/67 |
| 2007/0080017 | A1 * | 4/2007 | Stickley | 181/131 |
| 2007/0124972 | A1 * | 6/2007 | Ratcliffe | 40/591 |

* cited by examiner

STETHOSCOPE WITH IDENTIFYING-PERSONALIZING RING

The present invention relates to a medical stethoscope head, diaphragm portion and identifying-personalizing ring for medical stethoscope head, in particular in which the diaphragm portion and the identifying-personalizing ring are replaceable.

A medical stethoscope is still basic equipment both for doctors and graduate nurses, which causes that their number in every day using is very big. In connection with that, the problem of identifying a stethoscope and its user (owner) in health service institutions has emerged, especially when stethoscopes are from one manufacturer.

According to observation of external appearance of known medical stethoscopes from different manufacturers results that it is difficult to notice the differences between most of them in external shapes and basic details, and many of them are exactly the same, even in very fine elements, although their manufacturers are located in different and often in very distant countries from each other. It is a result of imitation, approaching reduction of manufacturing costs and also using unified elements, manufactured in long series by specialized manufacturers. It especially applies to Y-shape tubes, which connect a head of stethoscope with its headset, elastic rings that fasten a diaphragm to diaphragm portion, soft diaphragm covers and headframes.

The misleading similarity of stethoscopes leads to consider inconveniences including unintentional exchange stethoscopes by their users, which results from difficulties in standing up of official stethoscopes from private ones, in identifying stethoscopes being the equipment of different departments of health service institution, in identifying of a stethoscope by its individual user in case when it is accidentally next to the same model, etc. An owner of stethoscope feels discomfort if he/she finds in his/her surrounding more exactly the same stethoscopes. Additionally, it is impossible to use medical stethoscopes by companies, e.g. pharmaceutical companies, for advertising and marking them in such a way, that they explicitly, except overprints on diaphragms or headset pipes, be standing out from equipment used in advertising campaign by other companies. It is also unsatisfied demand directed to stethoscopes' manufacturers for over conventional differentiation and/or decoration their products in relation to competitive products or even to products of the same kind.

They are known attempts to distinguish stethoscopes by using of different kind identifying-personalizing or decorating elements. US200100188 and publication of international patent application WO 01/13788 disclose decorated covers in a form of sleeves which are put on whole stethoscopes or on their parts connecting medical stethoscope head with headset, which sleeves have shape imitating of animals' heads and their purpose is to reduce a children stress which is connected with an examination.

U.S. Pat. No. 5,920,038 discloses medical stethoscope head comprising a diaphragm with graphical marking. The diaphragm can be exchangeable in a head and it can be selected depending on marking for given patient or user. This arrangement is designed mainly for examining children and its aim is reducing stress and aversion before examination.

US2004/0048539 discloses a cover on medical stethoscope head in a form of elastic net, preferably of knitted fabric, or elastic cover imitating an animal's head, which is put on stethoscope head. The task of a cover is a reduction of patient discomfort, especially a child, resulting from a contact of a cold stethoscope head with his/her body.

In 3M company offer on www.3M website Worldwide: United States:HealthCare can be found a description of ways for entering laser overprints, limited to 25 characters, on diaphragms and diaphragm of stethoscope heads.

Thus, in known arrangements, used previously to distinguish medical stethoscope head of the same kind, the purpose is to unified and unclear personalization or to positive impress with infant patients. However, there is no arrangements of medical stethoscope heads of the same kind, distinguished by features which would make possibility to distinct individualizing of each single piece in very different ways, depending on personal preferences of future user or exactly according to his/her dictation and depending on wishing of companies which would intend to use them in advertising campaigns. The previous arrangements of distinguishing of medical stethoscope head, except using removed decorative covers described in previously mentioned publications US2001001188, WO 01/13788 and US2004/0048539, are not suited to repeated procedures of cleaning, disinfections and sterilization, which are required for that kind of equipment. Generally, manufacturers do not allow dipping of medical stethoscope heads in any liquid or carry out steam sterilization and they only recommend external wiping with alcohol or soap solution in water and using low temperature sterilization with ethylene oxide. It causes many inconveniences. In case of accidental wetting of medical stethoscope head a stethoscope has to be delivered to authorize service, because of its construction the user is not able to dismantle it to remove a rest of liquid and dry it exactly. Medical stethoscope head have to be periodically cleaned internally by authorized service from dirt, which can get inside during keeping them in pocket or during transporting them in dusty medical bag. In case of necessity of sterilization, medical stethoscope head have to be subjected to very long and expensive low temperature sterilization processes with ethylene oxide and then 36 hours long ventilation processes in aeration chambers, which processes are available only at large hospitals.

From prior art, medical stethoscope head with exchangeable diaphragm portions, including a diaphragram, are known, but they are not able to remove above mentioned inconveniences completely, because they are screwed on threaded pins of stethoscope head body, then thus they are not fixed at the body in defined, always the same position in relation to axes of their inlet pipes. It makes impossible to right identifying-personalizing, in the context of general rules of designing, by putting on the heads individually designed distinguishing graphical and/or structural elements, e.g. such as personalizing structural elements, initials or users name, logo of company which uses a stethoscope in advertising campaigns, etc., which should not be located accidentally, but always in the same fixation in relation to axis of inlet pipe, which is often used by designers of personalizing elements as a reference point for a distribution of individual elements which distinguish a stethoscope head.

There is also market demands for such medical stethoscope heads, which, after providing with distinguishing elements, would give possibility to carry out cleaning and washing by their users and would be wholly subjected to high temperature sterilization, especially steam sterilization, as required.

Thus, an aim of the invention is providing a medical stethoscope head, a construction of which allows easy, distinct and possibly widest identifying-personalizing in relation to other medical stethoscope heads of the same kind, which are manufactured in series by the same manufacturer and easy identification by user or user's group.

Another aim of the invention is providing a medical stethoscope head, an appearance of which would be easy changeable, also at retailer or wholesaler point or by stethoscope user with simple and easy accessible tools.

Another aim of the invention is providing a medical stethoscope head, which could be subjected to easy visible and distinct identifying-personalizing, also at retailer or wholesaler point or by stethoscope user, according to their preferences and wishing, while it would be suited to complete dismantle by user to subject it, both as a whole and in dismantled condition, for cleaning and sterilization, what is obligatory for such kind of medical equipment, also in common accessible table top steam sterilizers.

Another aim of the invention is providing exchangeable, distinct identifying-personalizing means for medical stethoscope head, which is easy to mount at the medical stethoscope head according to individual wishing of a purchaser, at a retail point or by the user on his own.

Another aim of the invention is providing easy exchangeable head for medical stethoscope head, which makes possible distinct identifying-personalizing of individual stethoscopes, also at retailers, according to preferences and wishing of individual stethoscopes' users, and simultaneously it is adapted to cleaning and sterilization, including high temperature sterilization, especially steam sterilization, which is obligatory for that kind of medical equipment, including using common accessible table top steam sterilizers.

The aims of the invention are provided by medical stethoscope head having a body with an inlet pipe and at least one diaphragm portion provided with a diaphragm at its lower surface, characterized in that at least one identifying-personalizing ring provided with identifying-personalizing means is mounted in any area at upper surface of said diaphragm portion, opposite to said diaphragm.

Preferably, the identifying-personalizing ring of medical stethoscope head, at its surface adjacent to diaphragm portion, is provided with at least one locating element for explicit locating the identifying-personalizing ring in defined angular position in relation to an axis of said inlet pipe of said body.

In particular preferably, the identifying-personalizing ring of medical stethoscope head, at its at least one side surface, is provided with fastening element for disconnectable joining it to said diaphragm portion. Also preferably, identifying-personalizing ring, at its at least one of upper or lower surfaces, can be provided with at least one threaded hole, in which an fastening element for fixing the identifying-personalizing ring to diaphragm portion is situated. Especially, the identifying-personalizing ring can be composed of at least two separate members, and also it can be made of any material or set of materials, which are connected each other in any combination.

Preferably, the identifying-personalizing ring of said medical stethoscope head can be an integral part of elastic fastening ring holding said diaphragm.

The aims of the invention are provided by an identifying-personalizing ring for a medical stethoscope head, comprising an upper and lower surface and two side surfaces, outer and inner, characterized in that any identifying-personalizing means is placed at said upper surface and at least one locating element is placed at said lower surface adjacent to a diaphragm portion for explicit locating the identifying-personalizing ring in defined angular position in relation to an axis of said inlet pipe of said body.

In one embodiment, preferably, a fastening element, especially thread, catch or recess, for connecting it with a diaphragm portion is placed at said at least one side surface of identifying-personalizing ring. Additionally, a fastening element, which is in a form of a hole for placing screw or pin, is located at its lower surface.

In particular, identifying-personalizing ring can be composed of at least two members and, preferably, can be done with any material or set of materials, connected each other according to any combination.

Further, an elastic fastening ring, which is integral part of the identifying-personalizing ring, can be fastened to an external side surface of the identifying-personalizing ring.

The aims of the invention are provided by a medical stethoscope head comprising a body having an inlet pipe and at least one diaphragm portion, which is provided with diaphragm at its lower surface, and characterized in that said diaphragm portion, at its upper surface, opposite to a diaphragm, is provided with any identifying-personalizing means, and said diaphragm portion is disconnectable joined with said body by at least one locating-connecting means, allowing exchanging of a diaphragm portion and holding defined angular position of said diaphragm portion in relation to an axis of said inlet pipe of said body.

Said identifying-personalizing means of a diaphragm portion could be its area distinguished by any elements and by any techniques. Additionally, in the one embodiment of the invention said identifying-personalizing means is an identifying-personalizing ring which is placed in any area at an upper surface of a diaphragm portion and is provided with at least one locating element for explicit locating the identifying-personalizing ring in defined angular position in relation to an axis of said inlet pipe of said body.

For disconnectable joining diaphragm portion with said body, said medical stethoscope head can be provided with said locating-connecting means, which in particular is selected from a screw joint, pin joint, bayonet joint and snap joint.

The aims of the invention are provided by a diaphragm portion for a medical stethoscope head having concave lower surface, at which a diaphragm is fastened, and opposite upper surface, and characterized in that it is provided with any identifying-personalizing means at its upper surface, and is provided with at least one element for disconnectable joining it to a body of a medical stethoscope head, and further having at least one element for explicit locating the diaphragm portion in defined angular position in relation to an axis of an inlet pipe of a body, after mounting in a medical stethoscope head.

Preferably, said identifying-personalizing means of a diaphragm portion is an area which is distinguished by any elements and/or by any techniques.

Moreover, in the embodiment of the invention at the upper surface of said diaphragm portion an annular recess for placing an identifying-personalizing ring is formed.

It is the advantage of the invention that it is possible to change an appearance of the medical stethoscope head in a simple manner, either by fastening the exchangeable identifying-personalizing ring having identifying-personalizing means to upper surface of the diaphragm portion or by disconnected fastening of the exchangeable diaphragm portion provided with identifying-personalizing means. Such identifying-personalizing of the medical stethoscope head is possible not only by manufacturer, but, using simple tools, by the user or another service point. An user can select identifying-personalizing ring (or a diaphragm portion having identifying-personalizing means) from manufacturer catalogue of ready elements, can ask for putting additional identifying-personalizing means according to personal preferences or can order manufacturing of identifying-personalizing ring (or diaphragm portion having identifying-personalizing means) according to his own design using basic materials of stethoscope manufacturer.

It is the advantage of the invention that the medical stethoscope head, provided with an identifying-personalizing ring or a diaphragm portion having identifying-personalizing means, makes possible easy and univocal association the given stethoscope with its user and allows the identifying-personalizing of the particular model of the medical stethoscope head according to personal preferences of its future user on a day of purchasing or in the future. If those personal preferences changed, it would be possible easy exchange of identifying-personalizing ring because a manner of fastening both of the identifying-personalizing ring and diaphragm portion allows easy exchange for another one.

It is the advantage of the invention that the number of identifying-personalizing variants of the medical stethoscope head for distinguishing it from other pieces of the same kind is practically infinite, because the number of designs of identifying-personalizing means by using any technologies, materials and colors is infinite.

The above ensures to the user of the stethoscope a comfort of distinguishing his/her stethoscope from another pieces of the same model, satisfies his/her aesthetic and ambition requirements and allows the companies, which use stethoscopes in advertising campaign, individualizing the medical stethoscope head in such a way, that stethoscopes are significantly distinguished from the same models of stethoscopes, which are used in another campaigns.

The considerable advantage of the invention is that the medical stethoscope head, which is identified-personalized according to the invention, can be easy dismantle into individual elements directly by user using commonly accessible tools to subject it periodic cleaning, washing, disinfections and high temperature sterilization procedures, in generally accessible, in the condition of medical practice, table top steam sterilizers. The reassembling of the stethoscope head also has not be made in a specialized service point, because the structure of the head guarantees repeatable locations of all elements in relation to axis of the body inlet pipe of the medical stethoscope head.

The invention is described by the exemplary embodiments with referring to the drawings, in which.

Figure 1:
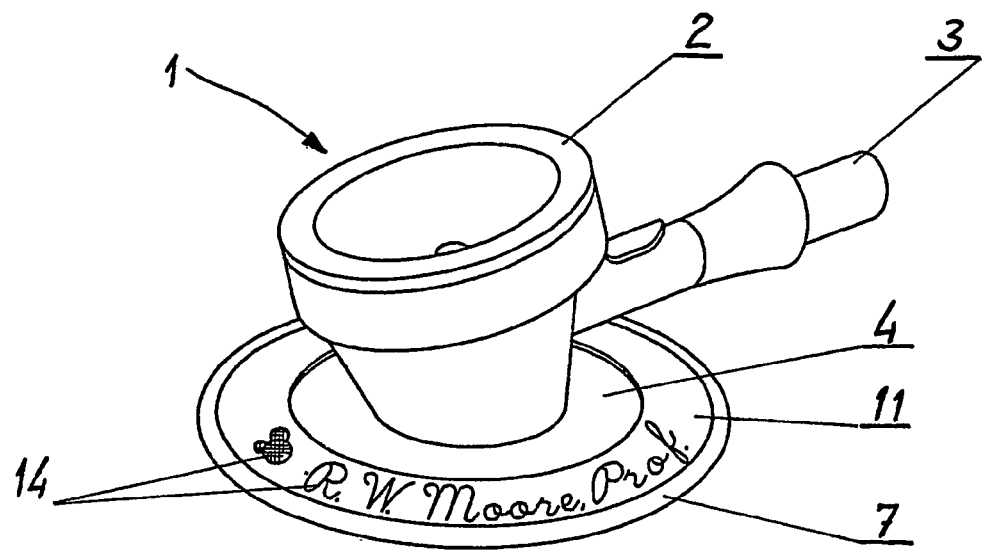
FIG. 1 is a perspective view of a first embodiment of the medical stethoscope head having an identifying-personalizing ring seated on it according to the invention.
Figure 2:
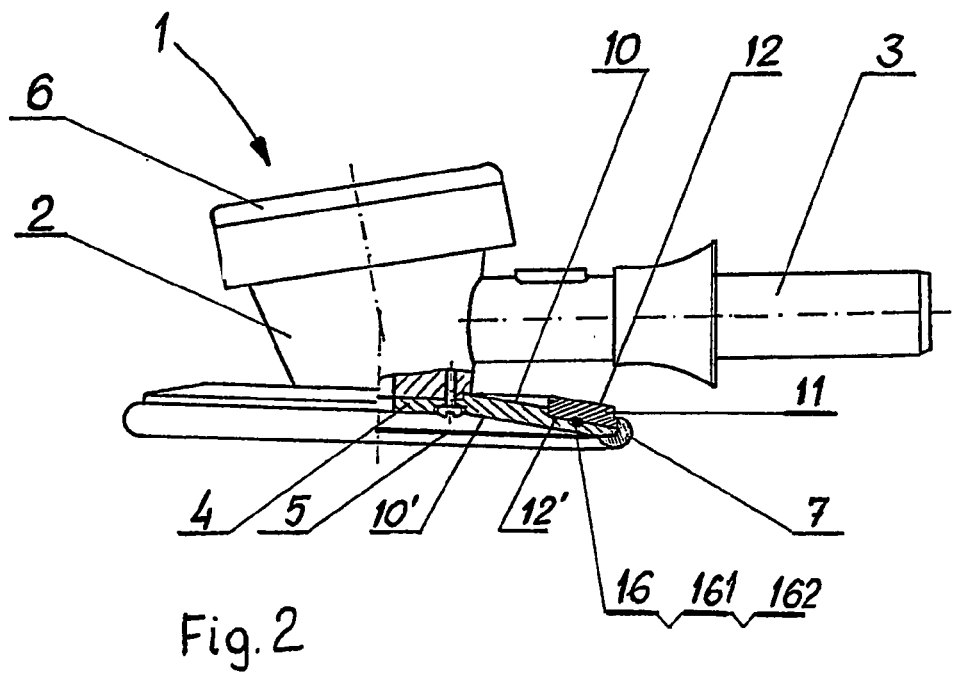
FIG. 2 is medical stethoscope head according to FIG. 1, in a side view and partly in cross section.
Figure 3:
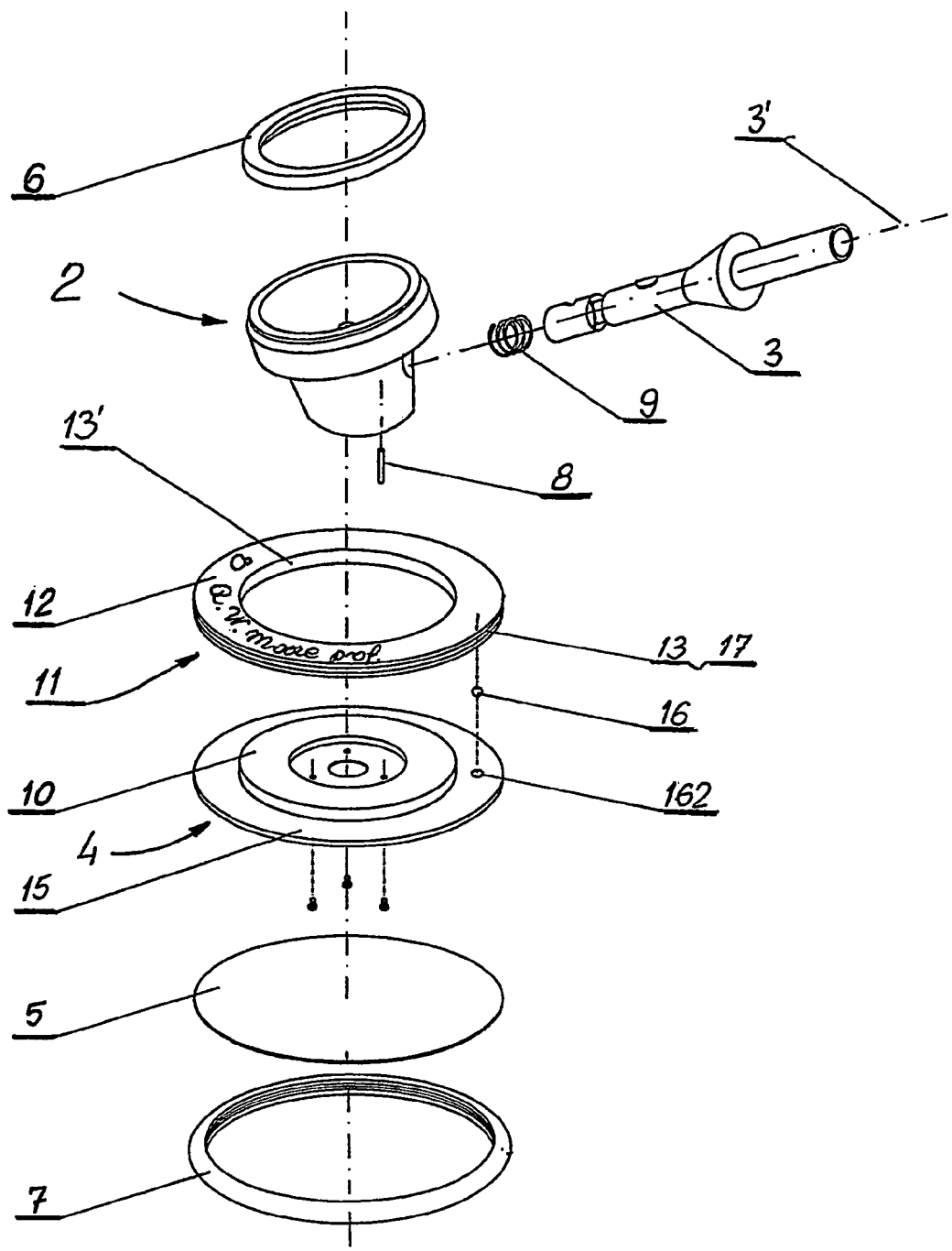
FIG. 3 is exploded view of the medical stethoscope head according to FIGS. 1 and 2, in perspective view.

In preferred embodiment in FIG. 1-3, a medical stethoscope head comprises a body 2 having an inlet pipe 3 and diaphragm portion 4 with diaphragm 5 (shown in FIG. 2-7). In presented embodiment, the body 2 is provided with insulation ring 6. The diaphragm 5 is hold at a diaphragm portion with fastening ring 7, and inlet pipe is seated in the body 2 by a pin 8 and a helical spring 9. The medical stethoscope head 1 can have any shape, such as, for instance, cardiologist, internist, pediatrician medical stethoscope heads, and like.

According to the invention, at an upper surface 10 of the diaphragm portion 4 of the medical stethoscope head 1, opposite to lower surface 10' adjacent to diaphragm 5, a identifying-personalizing ring 11 having an upper surface 12, a lower surface 12', and outer 13 and inner 13' side surfaces is mounted. The identifying-personalizing ring is a separate element and is fastened in free selected area of the upper surface 10 of the diaphragm portion 4 in fixed position in relation to an axis 3' of the inlet pipe 3. The identifying-personalizing ring 11 comprises identifying-personalizing means 14, which can be, especially, distinguishing surface texture or color of entire identifying-personalizing ring 11 and/or different kind of identifying personalizing marks located at its upper surface, such as overprints, engraved emblems and inscriptions, fastened decorated elements at part or entire its upper surface, a shape of its upper surface and the like. These identifying-personalizing means 14 can be selected individually according to wishing of a stethoscope user and they can be made at either completed identifying-personalizing rings 11 at manufacturer of a medical stethoscope head or at sale points, with using basic manufacturer's element.

The identifying-personalizing ring 11 in an embodiment in FIGS. 2, 3 is mounted at an upper surface 10 of the diaphragm portion 4, especially in recess 15 matched with shape and size to a shape and size of the identifying-personalizing ring 11 and situated, wholly or partly, the identifying-personalizing ring 11. In the embodiment of FIG. 1-3, the recess 15 extends from a circumferential edge of the diaphragm portion 4 radially to its center. To set of exact angular position of the identifying-personalizing ring 11 at the diaphragm portion 4 in relation to the axis 3' of the inlet pipe 3, and thus to explicitly define position of identifying-personalizing means 14 at the diaphragm portion 4, the identifying-personalizing ring 11 is provided with at least one locating element 16 for placing it in explicitly fixed angular position in relation to axis 3' of the inlet pipe 3. In the embodiment in FIGS. 1-3, the locating element 16 is in a form of a metal sphere, a lower part of which is fixed or removable mounted in a seat 162 at the upper surface 10 of the diaphragm portion 4, and its upper part is mounted in a seat 161 (shown in FIG. 2) provided in a lower surface 12' of the identifying-personalizing ring 11.

In the embodiment of FIGS. 2, 3, the outer side surface 13 of the identifying-personalizing ring 11 comprises fastening element 17, which is in a form of a thread, and the fastening ring 7 having a thread on its internal surface and supporting the diaphragm 5 at the diaphragm portion 4 is screwed on said thread. In such a manner, the identifying-personalizing ring 11 and the diaphragm 5 is simultaneously kept at the diaphragm portion 4.

FIGS. 4-7 show other preferable variants of fastening the identifying-personalizing ring 11 at the diaphragm portion 4.

Figure 4:
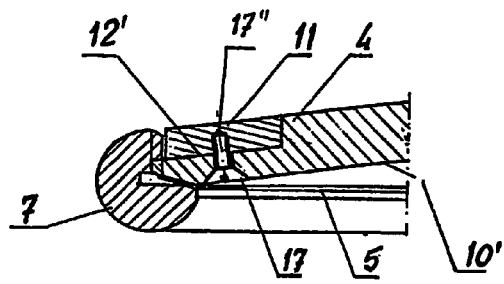
FIG. 4 to 7 are cross section of a subsequent modifications of first embodiment of the medical stethoscope head, showing alternative structures of the identifying-personalizing ring and its fastening to a diaphragm portion.

In a variant shown in FIG. 4, the identifying-personalizing ring 11 is fastened to the diaphragm portion 4 with at least one fastening element 17 being in a form of a screw which is entered from underside to an aperture in the diaphragm portion and screwed in a threaded hole 17" in a lower surface 12' of the identifying-personalizing ring 11. In this case the screw is simultaneously a locating element. In that embodiment, the fastening ring 7 is not connected to the identifying-personalizing ring 11.

Figure 4A:
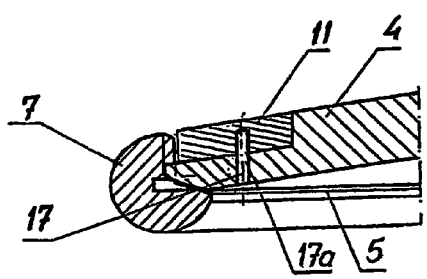

In the variant shown in FIG. 4a, the identifying-personalizing ring 11 is fastened to the diaphragm portion 4 by at least one fastening element 17 in a form of a pin, which is tightly seated in a aperture 17a of the diaphragm portion 4 and in a blind hole in a lower surface 12' of the identifying-personalizing ring 11. In this case, a pin, which constitutes a fastening element 17, together with the holes, is simultaneously a locating element.

Figure 4B:
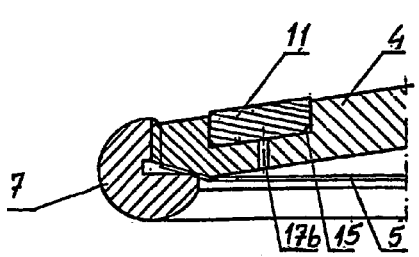

In the variant in FIG. 4b, the identifying-personalizing ring 11 is fastened with keying fit in a circumferential recess 15 of the diaphragm portion 4 and the circumferential recess 15 is located distal from the diaphragm portion side surface. The diaphragm portion 4 is provided with apertures 17b cooperating with a locating element for the identifying-personalizing ring 11 in a suitable angular position in relation to axis 3' of the inlet pipe 3 and designed to receiving a pushing pin for the identifying-personalizing ring 11 when it is needed to remove it from the diaphragm portion 4.

Figure 5:
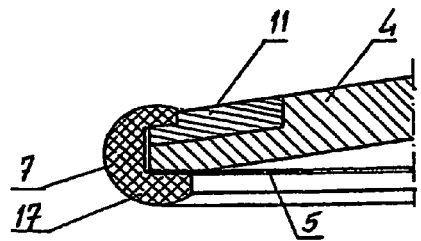

In the variant shown in FIG. 5, the identifying-personalizing ring 11 is fastened to the diaphragm portion 4 by fastening element 17 in a form of elastic fastening ring 7, which tightly encloses a lower edge of the diaphragm 5, a side surface of the diaphragm portion 4 and overlaps at upper surface 12 of the identifying-personalizing ring 11. Preferably, the rim of the identifying-personalizing ring 11 is shaped an offset surface, in which an upper part of the elastic fastening ring 7 is situated.

Figure 6:
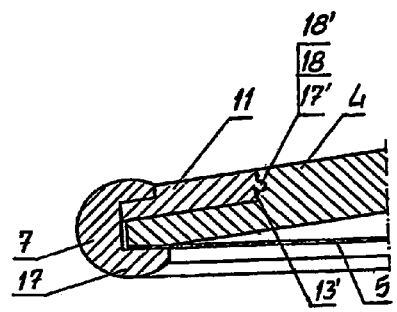

FIG. 6 shows an embodiment of the medical stethoscope head similar to those from FIG. 5, wherein an elastic fastening element is connected with the outer side surface of the identifying-personalizing ring 11 and it forms an integral part therefore being simultaneously a fastening ring 7 for a diaphragm 5.

The inner side surface 13' of the identifying-personalizing ring 11 is provided with additional fastening element 17' in a form of continuous or intermittent circumferential protrusion 18, located in a groove 18' formed in a side surface of the recess 15 for the identifying-personalizing ring 11 in the diaphragm portion 4. The additional fastening element 17' provides holding of the identifying-personalizing ring 11 and fastening ring 7 at the diaphragm portion 4.

Figure 7:
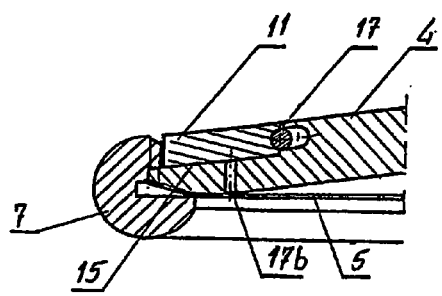

FIG. 7 presents a subsequent embodiment of the medical stethoscope head, which comprises the identifying-personalizing ring 11 fastened to the diaphragm portion 4 by a fastening element 17 in a form of spring ring. The spring ring is located in a seat formed between the identifying-personalizing ring 11 and the diaphragm portion 4. The seat for the spring ring is in a form of circumferential groove in an inner side surface 13' of the identifying-personalizing ring 11 and a circumferential groove in a side surface of the recess 15 in the diaphragm portion 4. The outer side surface 13 of the identifying-personalizing ring 11 contacts with a fastening ring 7 supporting the diaphragm 5. In such arrangement, the diaphragm portion 4 is provided with at least one aperture 17b, which cooperates with the element locating the angular position of the identifying-personalizing ring and is made between upper 10 and lower 10' surfaces of the diaphragm portion 4. The aperture 17b allows pushing the identifying-personalizing ring 11 out and separating it from the diaphragm portion 4 as a result of pushing it out with a tool in a form of a pin.

In each case, the identifying-personalizing ring 11 can be in one piece or it can be sectioned and it can compose from any number of members, if it is possible to keep them at a surface of the diaphragm portion 4 to form identifying-personalizing means.

Of course, in FIGS. 1-7 the embodiments both the identifying-personalizing ring 11 and its fastening and locating elements are only exemplary. The skilled person in the art can image many different elements for fastening the identifying-personalizing ring 11 and for fixing position of the identifying-personalizing ring 11 in relation to an axis 3' of inlet pipe 3 of the medical stethoscope head 1 such as elements of different snap and pin connection and the like. In specific cases, the identifying-personalizing ring 11 can be glued to the diaphragm portion 4.

Figure 8:
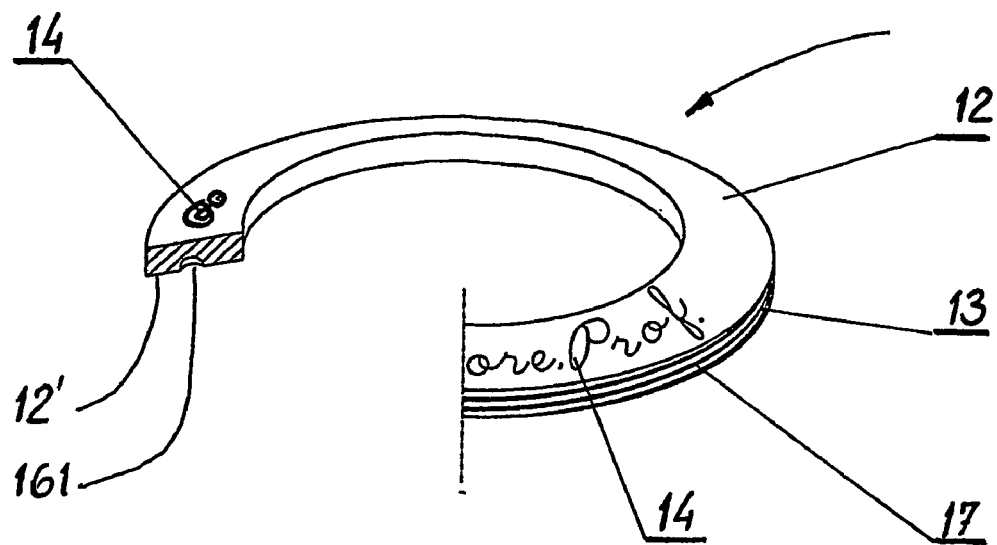
FIG. 8 is an embodiment of the identifying-personalizing ring, in perspective view, partly in cross section.

FIG. 8 shows the identifying-personalizing ring 11 according to the invention being an enlargement view of the ring described in connection with FIGS. 2 and 3. The upper surface 12 of the identifying-personalizing ring 11 is provided with, for example, an engraved inscription and set of three decorative hemispheres of different diameters, and at its lower surface 12', designed to contact with the diaphragm portion 4, there is at least one locating element 16 for explicit, repeated locating an angular position of the identifying-personalizing ring 11 in relation to an axis 3' of the inlet pipe 3 of the body 2 after mounting the ring in the medical stethoscope head 1. In the embodiment in FIG. 8, a locating element is a seat 161 formed in a lower surface 12' of the identifying-personalizing ring 11, designed for receiving a sphere 16 (shown in FIGS. 2 and 3). The outer side surface 13 is provided with fastening element 17 in a form of a thread for holding the identifying-personalizing ring 11 at the diaphragm portion 4 by threaded fastening ring 7 for fastening the diaphragm 5.

The identifying-personalizing ring 11 of the medical stethoscope head 1 according to the invention can be designed in such a manner as is described in reference to FIGS. 4-7. As it is shown, an element for fastening the identifying-personalizing ring 11 to the diaphragm portion 4 can be, e.g. at least one catch, thread or recess located at side surfaces 13, 13' or hole for placing screw or pin located at lower surface 12'.

As it is seen in FIG. 6, additional elastic ring, which is an integral part of the identifying-personalizing ring 11, can be attached to its outer side surface 13. The elastic ring functions as an element for fastening the identifying-personalizing ring 11 to the diaphragm portion 4 as well as a fastening ring 7 supporting the diaphragm 5.

The identifying-personalizing ring 11 can be made of any material or combination of materials, which are connected in any combination provided that they meet requirements referred to cleaning and sterilizing of the medical stethoscope head.

The identifying-personalizing ring 11 can have any width and thickness, it can be made as single layer or multi layer, in single color or in combination of many colors, of one or more materials that are connected in any combination. Its upper surface 12 can be in any shape. Also, its side surfaces 13 and 13' can have any shape depending on a variant of its fastening to the diaphragm portion 4.

Figure 9:
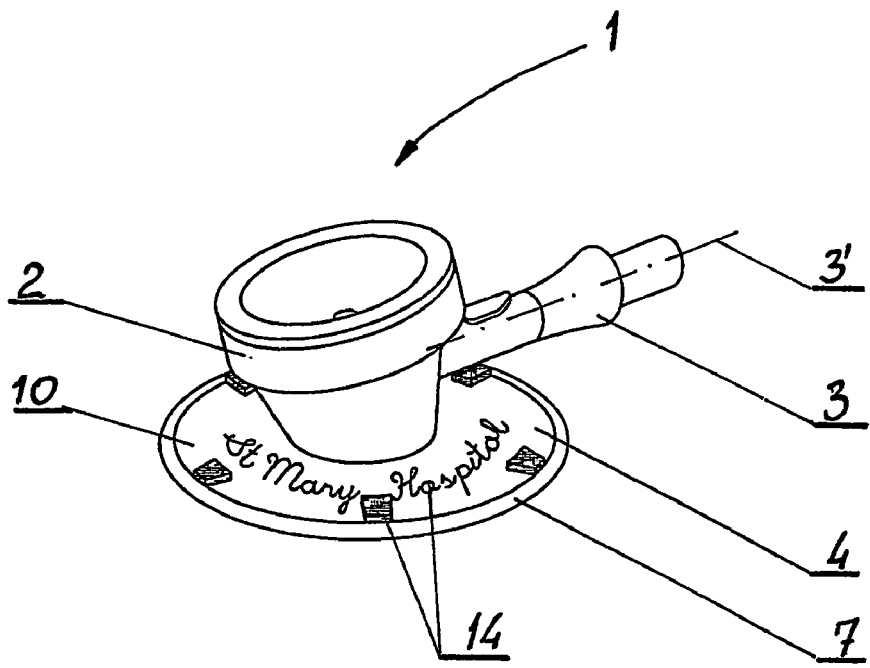
FIG. 9 is the second embodiment of the medical stethoscope head having identifying-personalizing element in a form of the diaphragm portion according to invention, in perspective view.
Figure 10:
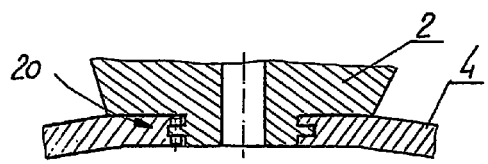
FIG. 10 to 20 are cross sections of subsequent modifications of the medical stethoscope head of FIG. 9, showing different preferable variants of locating-connecting unit of the diaphragm portion of a stethoscope head.
Figure 15:
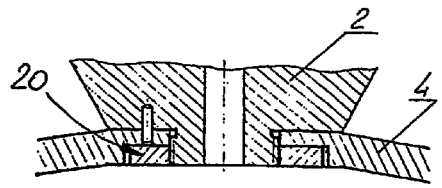

FIG. 9 shows a second embodiment of the medical stethoscope head 1, which, like in the embodiment shown in FIGS. 1-3 can have any shape and comprises the same parts. The difference is such that according to the invention, the medical stethoscope head 1 presented in FIG. 9 comprises the diaphragm portion 4, which at its upper surface 10, opposite to lower surface 10' adjacent to diaphragm (not shown) has the identifying-personalizing means 14 for distinguishing a medical stethoscope head from all other medical stethoscope heads of that kind. The identifying-personalizing means 14 comprises, for instance, engraved user name, and a set of color identifying-personalizing-decorating elements. Simultaneously, the diaphragm portion 4 is disconnectable join to a body 2 by at least one locating-fastening unit 20 allowing exchanging the diaphragm portion 4 and holding defined angular position of the diaphragm portion 4 in relation to an axis 3' of the inlet pipe 3 of the body 1.

The identifying-personalizing means 14 of the diaphragm portion 4 can be formed by an area distinguished by any method, for instance those which were described above in relation to the identifying-personalizing ring 11. The identifying-personalizing means 14 can be also formed by the identifying-personalizing ring 11 mounted in any area at an upper surface 10 of the diaphragm portion 4 and provided with at least one locating element for explicit locating its angular position in relation to an axis 3' of an inlet pipe 3 of a body 2.

FIGS. 10-20 shows different variants of the diaphragm portion 4 and a body 2. The medical stethoscope head of FIG. 10 comprises a locating-connecting unit 20 which is a bayonet connection.

Figure 11:
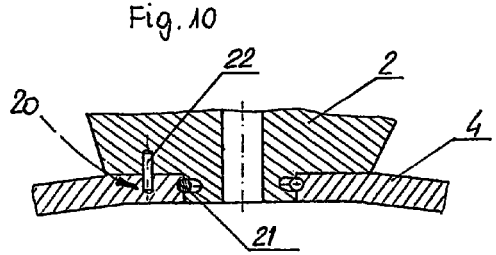
Figure 16:
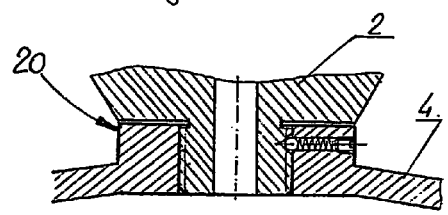

The medical stethoscope head in FIG. 11 comprises a locating-connecting means 20 comprising a fastening circumferential spring ring, which is placed partly in the joining element 21, in form of a groove, of the diaphragm portion 4 and partly in the joining element, in form of a groove, of the body 2. The locating-connecting means 20 comprises also at least one axially positioned locating pin placed in the locating element 22, in form of aperture, of the diaphragm portion 4.

Figure 12:
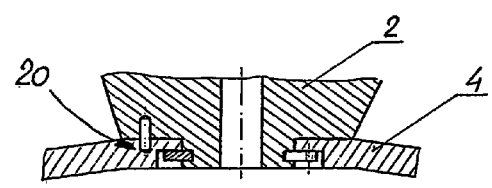
Figure 17:
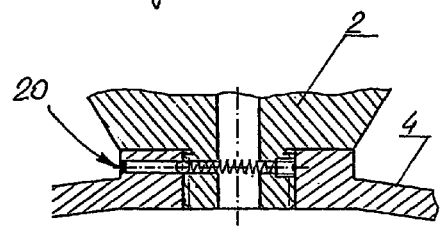
Figure 13:
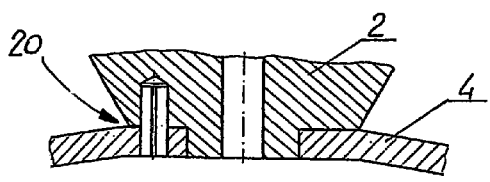
Figure 18:
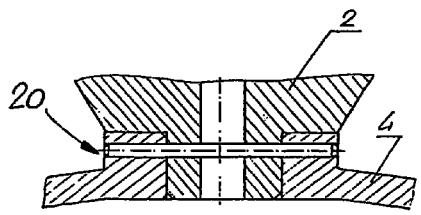
Figure 14:
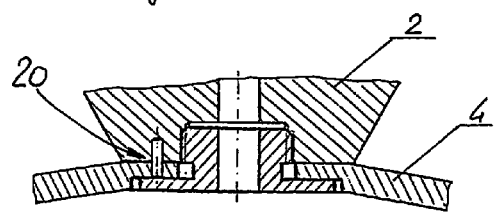
Figure 19:
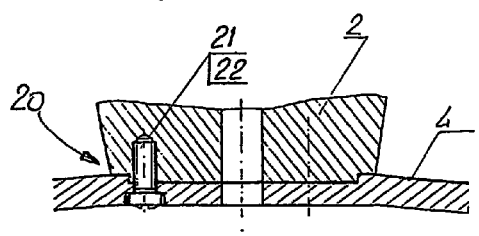
Figure 20:
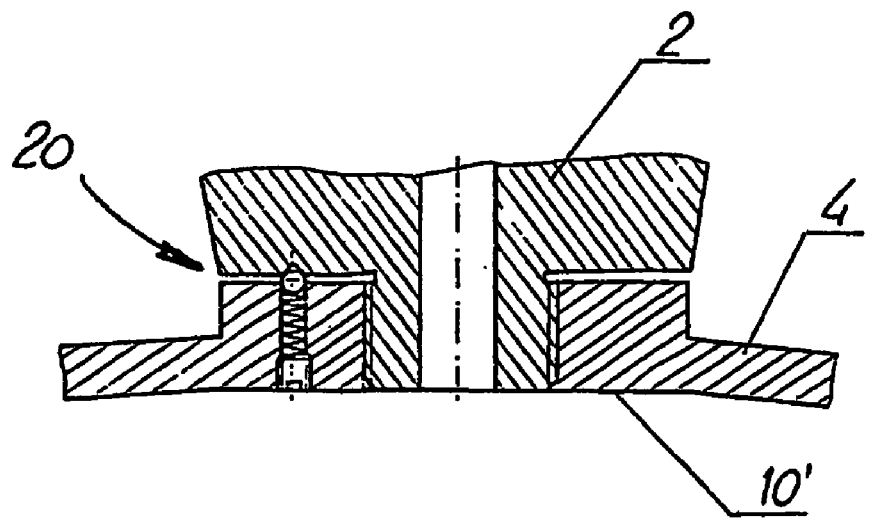

The medical stethoscope head in FIG. 12 has a locating-connecting means 20 comprising a fastening circumferential locking ring and at least one axial locating pin. The medical stethoscope head from FIG. 13 comprises a locating-connecting means 20 in form of at least one an axially positioned expanding pin. The medical stethoscope head from FIG. 14 has a locating-connecting means 20 comprising a positioned centrally bolt, which is axially fastened and at least one axial locating pin. The medical stethoscope head shown in FIG. 15 comprises a locating-connecting means 20 in a form of a nut, which is mounted on threaded lower pin of a body 2 and at least one axial locating pin. The medical stethoscope head shown in FIG. 16 comprises locating-connecting means 20 having a threaded joint located between the diaphragm portion 4 and a body 2 and a catch, which is situated between the sides of the diaphragm portion 4 and a body 2. The medical stethoscope head from FIG. 17 comprises locating-connecting means 20 similar to that from FIG. 16, but in that case, a catch extends along full diameter of the threaded part of a body 2. The medical stethoscope head from FIG. 18 comprises locating-connecting means 20 having pin, which extends transversally by a protrusion of the diaphragm portion 4 and a body 2. The medical stethoscope head from FIG. 19 comprises, especially preferably, a locating-connecting means 20, the same as shown also in FIGS. 2 and 3, comprising axially positioned screws, which pass through the aperture, constitute joining elements 21 and locating elements 22 and formed in the diaphragm portion 4, and screwed into a body 2. The medical stethoscope head from FIG. 20 comprises a locating-connecting means 20 providing with a screwed joint between the diaphragm portion 4 and a body 2 and a catch positioned axially between the diaphragm portion 4 and a body 2.

The arrangements of locating-connecting means 20 presented above do not exhaust all possible structures, which are evident for a skilled persons. Each suitable mechanic structures can be used provided that they explicitly and repeatedly locate the diaphragm portion 4 in a defined angular position in relation to an axis 3' of the inlet pipe 3, provide disconnectable fastening the diaphragm portion 4 to a body 2 and give a possibility for exchanging of the diaphragm portion 4 by simple and easy available tools such that the exchange could be made in a retailer points and by the user.

Figure 21:
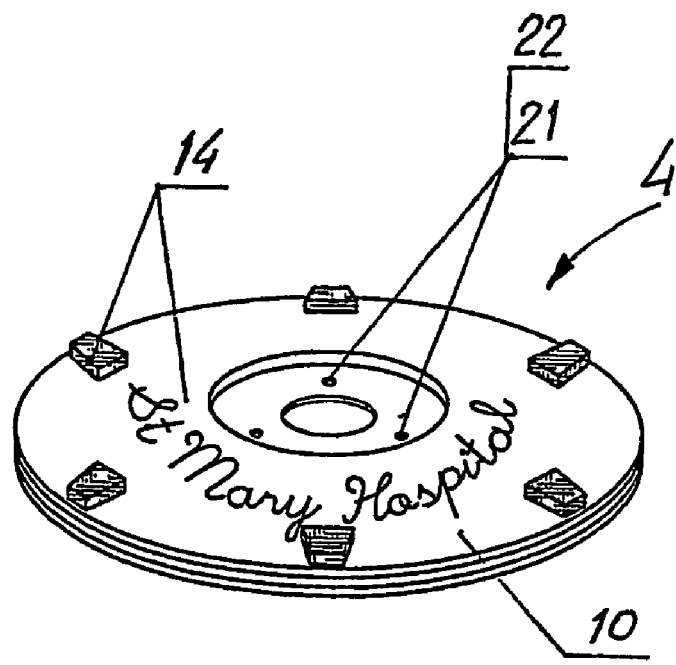
FIG. 21 is an perspective view exchangeable diaphragm portion for the medical stethoscope head of FIG. 9.

FIG. 21 shows one of possible embodiment of the exchangeable diaphragm portion for a medical stethoscope head. The diaphragm portion 4 comprises a concave lower surface 10', to which a diaphragm is fasten, and an opposite upper surface 10 provided with an identifying-personalizing means 14, which is composed of, for instance, user presenting inscription made by any method, and set of identical decorating-identifying-personalizing elements made of material which is different than remaining part of the diaphragm portion. The diaphragm portion includes three apertures, which constitutes joining elements 21 for screws, the same as in FIG. 19, which are designed both to fastening of the diaphragm portion 4 to a body 2 and for explicit locating the diaphragm portion 4 in defined angular in relation to 3' of the inlet pipe 3 of a body 2.

For instance, the identifying-personalizing means 14 of the diaphragm portion is an area distinguished by any elements and any method, like it was described in reference to an identifying-personalizing ring.

For instance, as an joining element 21 of the diaphragm portion 4 for attachment can be a hole for placing screws (best visible in FIG. 19), a groove for placing a spring ring (shown in FIG. 11), and a thread at surface of central hole in the diaphragm portion (FIG. 15) and like. An locating element 22 of the diaphragm portion 4 for establishing position can be in form of a hole for placing screw (FIG. 19) or pin (FIG. 11), a hole for placing a catch (FIG. 17), locating protrusions, etc.

At an outer surface of the diaphragm portion there is normally a thread for screwing a ring 7 on for fastening a diaphragm 5 or a circumferential recess, which is in a form of a catch for fastening of elastic ring for retaining a diaphragm.

In specially preferable embodiment, at an upper surface of the diaphragm portion 4 there is an annular recess for placing of the identifying-personalizing ring 11. The diaphragm portion 4 can comprise a one layer or more layers, it can be made of one or more materials connected in any combination. The shape of its upper surface 10 can be optional.

The invention was described with reference to the preferable embodiments which should not be treated in limited sense. The different modifications and variants of the presented arrangements are possible provided that they are covered by attached claims.

The invention claimed is:

1. A medical stethoscope head comprising:
a body;
an inlet pipe extending from said body and having an axis;
a diaphragm cup having an upper surface, a lower surface opposite to said upper surface and being removably secured to said body for allowing an exchange of said diaphragm cup;
a diaphragm held at said lower surface of said diaphragm cup by a fastening ring;
said stethoscope head further comprising:
at least one personalizing-identifying ring for distinguishing and identifying a stethoscope; said personalizing-identifying ring having an upper surface, a lower surface, an outer side surface, an inner side surface and said personalizing-identifying ring located with its lower surface on said upper surface of said diaphragm cup; the lower surface of said personalizing-identifying ring being provided with at least one locating element for explicitly locating said personalizing-identifying ring on said diaphragm cup;

means for locating and connecting said diaphragm cup to said body provided in said diaphragm cup and in said body and cooperating with each other for removably securing said diaphragm cup to said body in preset angular position in relation to said axis of said inlet pipe;

distinguishing means for personalizing and identifying the stethoscope provided on said upper surface of said at least one personalizing-identifying ring for distinguishing and identifying a stethoscope.

2. A medical stethoscope head according to claim 1, characterised in that a fastening element is provided on one of said side surface of said personalizing-identifying ring for removably secured said personalizing-identifying ring to said diaphragm cup.

3. A medical stethoscope head according to claim 1, characterised in that on one of its upper surface and lower surface said personalizing-identifying ring is provided with at least one threaded hole in which a fastening element is situated for securing said personalizing-identifying ring to the diaphragm cup.

4. A medical stethoscope head according to claim 2, characterised in that said fastening element is in the form of thread, catch or recess.

5. A medical stethoscope head according to claim 1, characterised in that said fastening ring is elastic and said personalizing-identifying ring is formed integrally with said fastening ring.

6. A medical stethoscope head according to claim 1, characterised in that said positioning-connecting means is selected from a screwjoint, pin joint, bayonet joint and snap joint.

7. A medical stethoscope head according to claim 1, wherein an annular recess is formed on the upper surface of said diaphragm cup for placing said personalizing-identifying ring.

* * * * *